US00PP30646P2

(12) United States Plant Patent
Mak

(10) Patent No.: US PP30,646 P2
(45) Date of Patent: Jul. 2, 2019

(54) LILY PLANT NAMED 'MIRACLE'

(50) Latin Name: *Lilium longiflorum*
Varietal Denomination: Miracle

(71) Applicant: Niels Johannes Cornelis Mak, Wieringerwerf (NL)

(72) Inventor: Niels Johannes Cornelis Mak, Wieringerwerf (NL)

(73) Assignees: Mak Breeding Rights B.V., Wieringerwerf (NL); Arroyo Rights B.V., Den Hoorn (NL)

( * ) Notice: Subject to any disclaimer, the term of this patent is extended or adjusted under 35 U.S.C. 154(b) by 0 days.

(21) Appl. No.: 15/999,916

(22) Filed: Aug. 29, 2018

(51) Int. Cl.
*A01H 5/02* (2018.01)
*A01H 6/56* (2018.01)

(52) U.S. Cl.
USPC ..... Plt./313
CPC ..... *A01H 6/56* (2018.05); *A01H 5/02* (2013.01)

(58) Field of Classification Search
USPC ..... Plt./313
CPC ..... A01H 5/0272
See application file for complete search history.

*Primary Examiner* — Kent L Bell
(74) *Attorney, Agent, or Firm* — C. A. Whealy

(57) ABSTRACT

A new and distinct cultivar of Lily plant named 'Miracle', characterized by its relatively compact and upright plant habit; vigorous growth habit; freely flowering habit; large pure white-colored flowers that face outwardly; and good postproduction longevity.

1 Drawing Sheet

Botanical designation: *Lilium longiflorum.*
Cultivar denomination: 'MIRACLE'.

BACKGROUND OF THE INVENTION

The present Invention relates to a new and distinct cultivar of Lily plant, commercially referred to as Easter or Trumpet Lily, botanically known as *Lilium longiflorum* and hereinafter referred to by the name 'Miracle'.

The new Lily plant is a product of a planned breeding program conducted by the Inventor in Wieringerwerf, The Netherlands. The objective of the breeding program is to develop new freely-flowering Lily plants with pure white-colored flowers and good postproduction longevity.

The new Lily plant originated from a cross-pollination in June, 2006 of two unnamed proprietary seedling selections of *Lilium longiflorum*, not patented. The new Lily plant was discovered and selected by the Inventor as a single flowering plant from within the resultant progeny of the stated cross-pollination in a controlled greenhouse environment in Wieringerwerf, The Netherlands in June, 2009.

Asexual reproduction of the new Lily plant by bulb scales in a controlled greenhouse environment in Wieringerwerf, The Netherlands since June, 2009 has shown that the unique features of this new Lily plant are stable and reproduced true to type in successive generations.

SUMMARY OF THE INVENTION

Plants of the new Lily have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Miracle'.

These characteristics in combination distinguish 'Miracle' as a new and distinct Lily plant:

1. Relatively compact and upright plant habit.
2. Vigorous growth habit.
3. Freely flowering habit.
4. Large pure white-colored flowers that face outwardly.
5. Good postproduction longevity.

Plants of the new Lily differ primarily from plants of the female parent selection in the following characteristics:

1. Plants of the new Lily are taller than plants of the female parent selection.
2. Leaves of plants of the new Lily are shorter than leaves of plants of the female parent selection.
3. Plants of the new Lily are more freely flowering than plants of the female parent selection.

Plants of the new Lily differ primarily from plants of the male parent selection in the following characteristics:

1. Plants of the new Lily are more compact than plants of the male parent selection.
2. Plants of the new Lily have larger flower buds than plants of the male parent selection.

Plants of the new Lily can be compared to plants of the Lily 'White Heaven', not patented. Plants of the new Lily differ from plants of 'White Heaven' in the following characteristics:

1. Plants of the new Lily are typically grown as potted plants whereas plants of 'White Heaven' are typically grown as cut flower plants.
2. Plants of the new Lily have smaller flower buds and flowers than plants of 'White Heaven'.
3. Tepals of plants of the new Lily are not as recurved as tepals of plants of 'White Heaven'.

DESCRIPTION OF THE PHOTOGRAPH

The accompanying colored photograph illustrates the overall appearance of the new Lily plant showing the colors as true as it is reasonably possible to obtain in colored reproductions of this type. Colors in the photograph may differ slightly from the color values cited in the detailed botanical description which accurately describe the colors of the new Lily plant.

The photograph comprises a side perspective view of typical flowering plants of 'Miracle' grown in containers.

DETAILED BOTANICAL DESCRIPTION

The aforementioned photograph and following observations and measurements describe plants grown during the spring in 15-cm containers in a glass-covered greenhouse in Wieringerwerf, The Netherlands and under cultural practices typically used in commercial production. During the production of the plants, day temperatures averaged 18° C., night temperatures averaged 15° C. and light levels averaged 6,000 lux. Measurements and numerical values represent averages for typical flowering plants. Plants were 110 days old when the photograph and description were taken. In the following description, color references are made to The Royal Horticultural Society Colour Chart, 2015 Edition, except where general terms of ordinary dictionary significance are used.

Botanical classification: *Lilium longiflorum* 'Miracle'.

Parentage:

*Female, or seed, parent*.—Unnamed proprietary seedling selection of *Lilium longiflorum*, not patented.

*Male, or pollen, parent*.—Unnamed proprietary seedling selection of *Lilium longiflorum*, not patented.

Plant description:

*Plant and growth habit*.—Upright plant habit; single erect flowering stem with a terminal cluster of flowers; relatively compact and dense plant habit; vigorous growth habit.

*Plant height, soil level to top of flowers*.—About 30 cm.

*Plant diameter or spread*.—About 14 cm.

*Plant circumference*.—About 42 cm.

*Bulbs*.—Diameter: About 10 cm to 20 cm. Texture: Smooth. Color: Close to 155D.

*Flowering stems*.—Diameter: About 1.3 cm. Internode length: About 1.2 cm to 2 cm. Strength: Strong. Texture: Smooth, glabrous. Color: Close to 135A.

*Leaves*.—Arrangement: Alternate, simple; sessile; about 50 leaves develop per plant. Length, upper leaves: About 12.5 cm. Width, upper leaves: About 3.5 cm. Length, lower leaves: About 10 cm. Width, lower leaves: About 7 mm. Shape: Lanceolate. Apex: Acute. Base: Acutely cuneate. Margin: Entire. Aspect: Mostly horizontal, flat. Texture and luster, upper and lower surfaces: Glabrous, smooth; leathery; moderately glossy. Venation pattern: Parallel. Color: Developing and fully expanded leaves, upper surface: Close to 135A; venation, close to 135A. Developing and fully expanded leaves, lower surface: Close to 135A; venation, close to 135A.

Flower description:

*Flower shape and aspect*.—Flowers umbellate and trumpet-shaped; when fully opened, tepals slightly to moderately recurved; flower buds and flowers face outwardly.

*Flowering habit*.—Freely flowering habit, large bulbs will produce up to five flowers per flowering stem.

*Fragrance*.—Slightly fragrant; sweet, pleasant.

*Natural flowering season*.—Plants flower in June and July in The Netherlands; plants can be flowered year-round in the greenhouse and forced to bloom about 110 days after planting bulbs.

*Postproduction longevity*.—Good postproduction longevity, flowers last about two weeks on the plant; tepals not persistent; gynoecium persistent.

*Flower buds*.—Length: About 15 cm. Diameter: About 4.5 cm. Circumference: About 14.5 cm. Shape: Lanceolate. Color: Close to between 145C and 149D; sutures, close to 144D.

*Flower size*.—Diameter: About 15 cm. Length (height): About 15 cm.

*Perianth*.—Quantity and arrangement: Six tepals per flower arranged in two whorls; tepals imbricate. Tepal length, inner tepals: About 15 cm. Tepal width, inner tepals: About 6 cm. Tepal length, outer tepals: About 15 cm. Tepal width, outer tepals: About 4.5 cm. Tepal shape: Lanceolate. Tepal apex: Acute, slightly to moderately recurved. Tepal margin: Entire. Tepal texture, upper and lower surfaces: Smooth, glabrous. Tepal color: When opening and fully opened, upper surface: Close to NN155C; proximally, close to 157D; color does not change with development. When opening and fully opened, lower surface: Close to NN155C; proximally, close to 157D; color does not change with development. Throat: Close to 143B; nectar furrow, close to 140C.

*Pedicels*.—Length: About 7 cm. Diameter: About 1 cm. Angle: About 90° to 95° from flowering stem. Strength: Strong. Texture: Smooth, glabrous. Color: Close to 135A.

*Reproductive organs*.—Stamens: Quantity per flower: Six. Filament length: About 10 cm. Filament color: Close to 145D. Anther length: About 1.2 cm. Anther color: Close to 145D. Pollen color: Close to 17B. Pistils: Quantity per flower: One. Style length: About 10 cm. Style color: Close to 145D.

*Fruits*.—Length: About 3 cm. Diameter: About 7 mm. Color: Close to 141D.

*Seeds*.—To date, no viable seeds have been observed on plants of the new Lily.

Disease & pest resistance: To date, resistance to pathogens and pests common to Easter Lilies has not been observed on plants of the new Lily.

Garden performance: Plants of the new Lily have exhibited good tolerance to rain and wind and have been observed to tolerate temperatures from about 5° C. to about 30° C.

It is claimed:

1. A new and distinct Lily plant named 'Miracle' as illustrated and described.

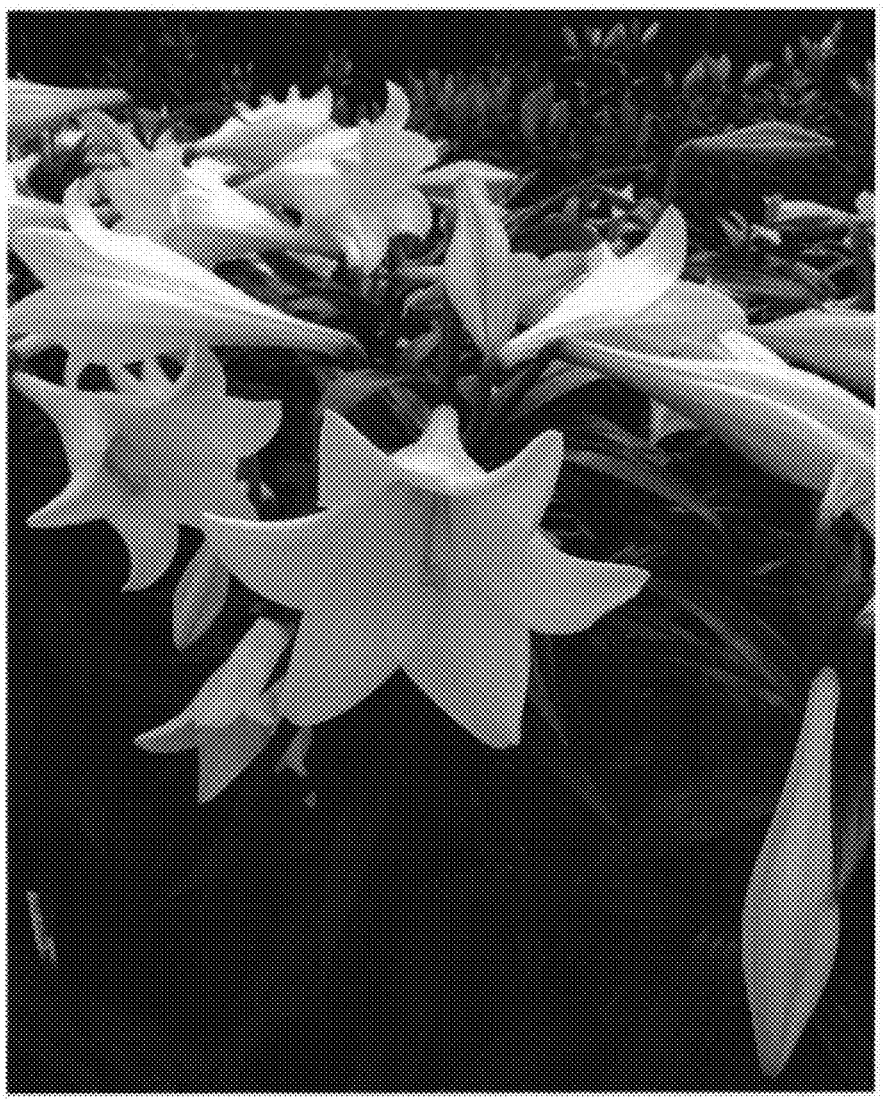

* * * * *